US 6,682,499 B2
Jan. 27, 2004

(54) METHOD AND APPARATUS FOR VENOUS DRAINAGE AND RETROGRADE CORONARY PERFUSION

(76) Inventor: Jay Alan Lenker, 408 Panorama Dr., Laguna Beach, CA (US) 92651

( * ) Notice: Subject to any disclaimer, the term of this patent is extended or adjusted under 35 U.S.C. 154(b) by 0 days.

(21) Appl. No.: 09/894,564

(22) Filed: Jun. 28, 2001

(65) Prior Publication Data

US 2003/0004452 A1 Jan. 2, 2003

(51) Int. Cl.[7] .................. A61M 37/00; A61M 29/00; A61M 31/00
(52) U.S. Cl. ................. 604/4.01; 604/96.01; 604/503
(58) Field of Search .................. 604/96.01, 503, 604/4.01

(56) References Cited

U.S. PATENT DOCUMENTS

| 5,021,045 A | | 6/1991 | Buckberg et al. | |
|---|---|---|---|---|
| 5,324,260 A | | 6/1994 | O'Neill et al. | |
| 5,385,548 A | * | 1/1995 | Williams et al. | 600/16 |
| 5,558,644 A | * | 9/1996 | Boyd et al. | 604/102.02 |
| 5,562,606 A | | 10/1996 | Huybregts | |
| 5,597,377 A | | 1/1997 | Aldea | |
| 5,620,418 A | | 4/1997 | O'Neill et al. | |
| 5,658,309 A | * | 8/1997 | Berthiaume et al. | 604/96.01 |
| 5,697,905 A | * | 12/1997 | d'Ambrosio | 604/27 |
| 5,707,358 A | | 1/1998 | Wright | |
| 5,800,375 A | * | 9/1998 | Sweezer et al. | 604/4.01 |
| 5,820,586 A | | 10/1998 | Booth et al. | |
| 5,919,163 A | * | 7/1999 | Glickman | 604/101.05 |
| 5,961,536 A | * | 10/1999 | Mickley et al. | 604/96.01 |
| RE36,386 E | | 11/1999 | Abbott et al. | |
| 6,099,498 A | | 8/2000 | Addis | |
| 6,110,139 A | | 8/2000 | Loubser | |
| 6,210,363 B1 | * | 4/2001 | Esch et al. | 604/96.01 |
| 6,398,752 B1 | * | 6/2002 | Sweezer et al. | 604/6.14 |

* cited by examiner

Primary Examiner—William C. Doerrler
Assistant Examiner—Filip Zec

(57) ABSTRACT

A system is disclosed for cannulating the vena cava of a patient during cardiopulmonary bypass procedures. Such cannulation is necessary for drainage of venous blood from the patient so that it may be oxygenated and pumped back to the patient to perfuse tissues during cardiac surgery and, more specifically, during periods of ischemic cardiac arrest or dysfunction. The device of the present invention not only provides venous drainage for cardiopulmonary bypass, but also performs the function of routing cardioplegic solution through the heart in the retrograde direction. Such cardioplegia provides protection to the heart during periods of ischemic cardiac arrest. This invention replaces a plurality of cannulae currently used for open-heart surgery, thus simplifying the surgical field and improving visibility of the heart.

6 Claims, 7 Drawing Sheets

METHOD AND APPARATUS FOR VENOUS DRAINAGE AND RETROGRADE CORONARY PERFUSION

FIELD OF THE INVENTION

The field of this invention is cardiac bypass surgery.

BACKGROUND OF THE INVENTION

During cardiac surgery for procedures such as coronary artery bypass grafting, heart valve repair or replacement, septal defect repair, pulmonary thrombectomy, atherectomy, aneurysm repair, aortic dissection repair and correction of congenital defects, cardiopulmonary bypass and cold cardiac ischemic arrest are often required. Typically, a cooled cardioplegia solution, a solution containing elevated levels of potassium, for example, is administered in the antegrade direction (in the direction of normal blood flow) through the patient's aorta and into the coronary arteries. The cold (2 to 3 degrees centigrade) cardioplegia solution stops the heart from beating and reduces its temperature to minimize damage to the heart during surgery. Cardiopulmonary bypass maintains the peripheral circulation of oxygenated blood to all body organs except the heart during the period of cold, cardioplegic, ischemic arrest.

For some patients, such as those suffering from critical coronary artery stenosis and aortic valve disease, antegrade perfusion may be difficult, inefficient and incomplete. Retrograde (in the direction opposite of normal blood flow) cardioplegia, using current technology, may be administered via the coronary sinus into the coronary circulation.

Currently surgeons performing cardiac bypass surgery use one or more cannulae for venous drainage and additional cannulae for retrograde perfusion. The multiple cannulae are obstacles and restrict visibility in the surgical arena. Placement of the cardioplegia cannula into the coronary sinus is a semi-blind procedure performed through an additional purse-string suture-closed access port via the right atrium. The retrograde cannula may be improperly positioned within the coronary sinus, which results in critical coronary vessels being inadequately perfused.

New devices and methods are needed, which facilitate cold cardioplegic arrest, yet limit the number of cannulae required to isolate the heart and coronary blood vessels from the peripheral vasculature, arrest the heart, protect all the coronary blood vessels, and drain venous blood from the inferior and superior vena cava.

SUMMARY OF THE INVENTION

This invention relates to a balloon, or tourniqueted, catheter or cannula useful in the retrograde administration of cardioplegia through the coronary sinus and simultaneous venous drainage during cardiac bypass surgery without the need to cannulate the coronary sinus.

The present invention is a cannula for performing venous drainage and retrograde perfusion of the heart during cardiac bypass surgery. A single multi-lumen cannula of the present invention can perform the same function as multiple cannulae. The cannula of the invention for cardioplegic administration can improve the protection of a heart during periods of ischemia such as occurs during open-heart surgery.

The present invention is a multi-lumen cannula with superior and inferior vena cava occlusion structures, cardioplegia infusion and drainage ports, a pressure monitoring port, and venous drainage ports. Typical occlusion structures may include balloons, umbrellas, or externally applied tourniquets. The preferred occlusion structures are balloons constructed of elastomeric materials.

A first lumen of the cannula is connected to the cardioplegia infusion system and provides cardioplegia solution to arrest the heart. A second cannula lumen is connected to the venous drainage system. The drainage ports are located in the second lumen. A third lumen is connected to the balloon inflation system, which provides inflation fluids, such as water, isotonic saline or cardioplegia solution, under controlled pressure or volume to inflate the balloons. The pressure of the balloons and right atrium may also be monitored through additional lumens. The balloons isolate the heart from the peripheral vasculature by occluding the inferior and superior vena cava just proximal to the right atrium. Additional lumens may be utilized for inflation of multiple balloons, pressure monitoring, flow monitoring, drainage of cardioplegia, fluid and drug infusion and the like. Since it is useful to measure cardioplegic perfusion pressure, a pressure transducer or pressure measuring lumen may be provided at or near the distal end of the cardioplegia perfusion lumen for this purpose.

The cannula is placed into the vena cava via a route through the internal jugular vein, cranial vena cava or brachial vein. A smaller diameter cannula could be placed through smaller venous access ports. The use of smaller venous access ports could be enabled by use of a pump or vacuum powered venous drainage system, typically external to the cannula. The catheter of the present invention combines the functions of several catheters currently used in cardiac surgery. This facilitates the surgery and improves the surgical field because extra cannulae do not obstruct the operative field. The number of individual catheters is reduced, providing a more cost effective method for cardiac surgery. Most importantly, improved cardiac protection is achieved compared to that of standard retrograde perfusion cannulae.

DETAILED DESCRIPTION OF THE INVENTION

Figure 1:
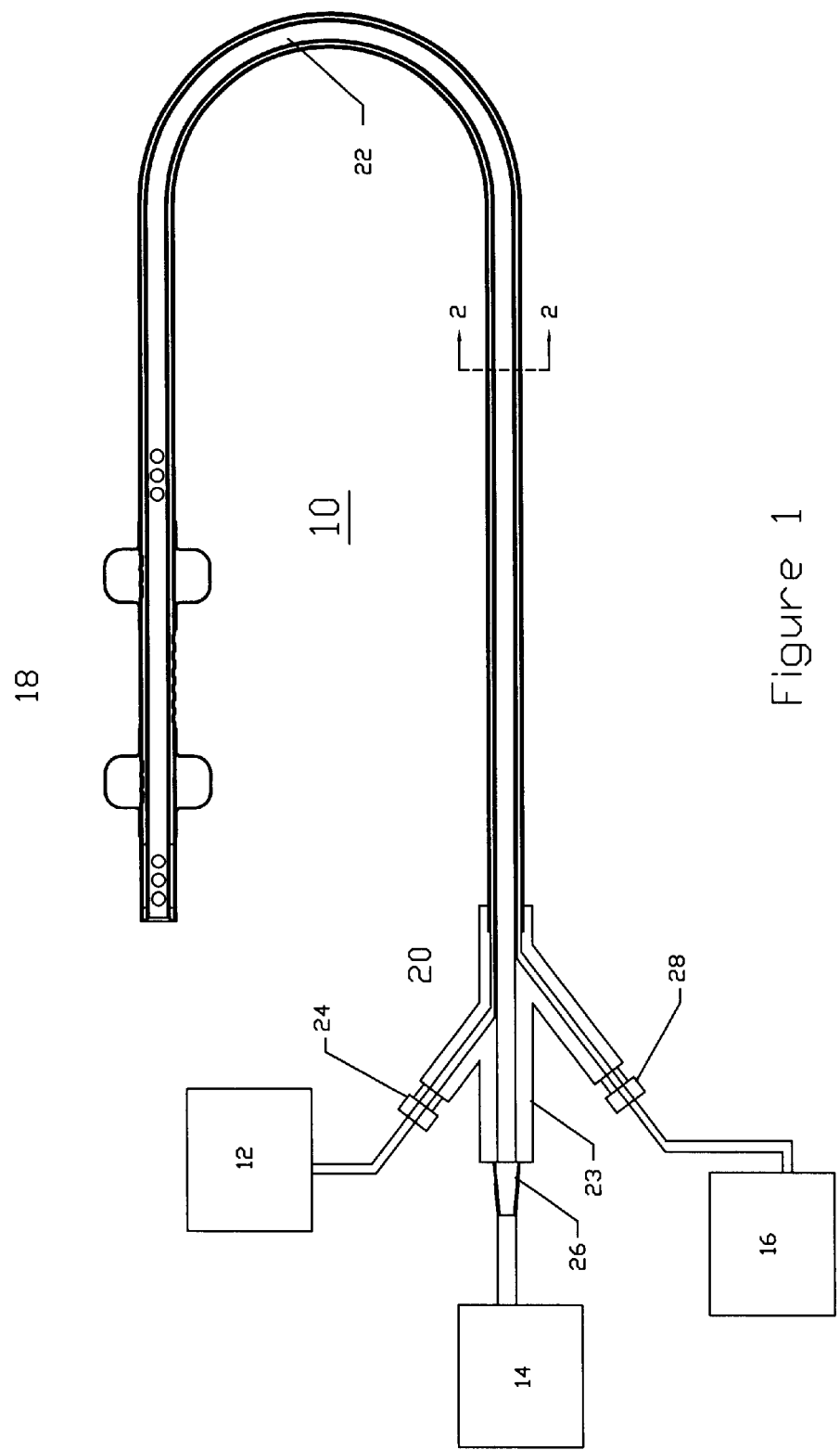
FIG. 1 illustrates a longitudinal cross-section of the cannula of the present invention comprising a distal tip, a proximal end, and a connecting tube according to aspects of an embodiment of the invention. External systems provide for venous drainage, cardioplegia infusion, and balloon inflation.

FIG. 1 illustrates a catheter, tube or cannula 10 of the present invention connected to a cardioplegia infusion system or set 12, a venous drainage collection system 14 and an occlusion enabling system 16. In this preferred embodiment, the occlusion enabling system 16 is a balloon inflation system. The catheter 10 comprises a distal tip 18, a proximal end 20, and a length of multi-lumen connection tubing 22. The proximal end 20 comprises a manifold or hub 23. The manifold 23 comprises a cardioplegia infusion adapter or fitting 24, a venous drainage collection adapter or fitting 26, and an occlusion adapter 28. In this preferred embodiment, the occlusion adapter 28 is a balloon inflation adapter or luer fitting. The manifold 23 is typically molded from polymer, such as polyvinyl chloride, polycarbonate, or the like.

The cardioplegia infusion adapter 24 is connected to the cardioplegia infusion system 12. The cardioplegia infusion adapter 24 may be any fluid-tight fitting, such as a luer fitting, suitable for use with the cardioplegia infusion set 12. The standard cardioplegia system 12 generally comprises a pressurized or non-pressurized bag of cardioplegia solution, a roller pump, a length of tubing and a plurality of connectors. Standard cardioplegia solutions include water, electrolytes such as but not limited to potassium, crystalloid solutions, and blood.

The venous drainage collection adapter 26 is connected to the venous drainage collection system 14. The drainage collection adapter 26 is typically larger in diameter than the balloon inflation fitting 28 or cardioplegia infusion fitting 24. The drainage collection adapter 26 should be capable of being connected to the gravity fed, pump driven or vacuum fed drainage system 14 and is most typically a ⅜ inch to ½ inch diameter hose barb. Standard venous drainage systems 14 generally comprise a connector, a length of tubing and a venous reservoir. Optionally, a vacuum pump may be connected to the venous reservoir.

The balloon inflation adapter 28 is connected to the balloon inflation system 16. The balloon inflation adapter 28 is typically a female luer fitting but may be any fluid-tight fitting suitable for use with an inflation syringe or the like. The standard balloon inflation system 16 comprises a syringe, a volume of balloon inflation fluid such as saline or radiopaque media, and a valve or stopcock associated with each balloon inflation adapter 28. Additionally, the balloon inflation system 16 could comprise a device, such as a jackscrew, to advance or withdraw a plunger on the syringe using mechanical advantage.

Figure 2:
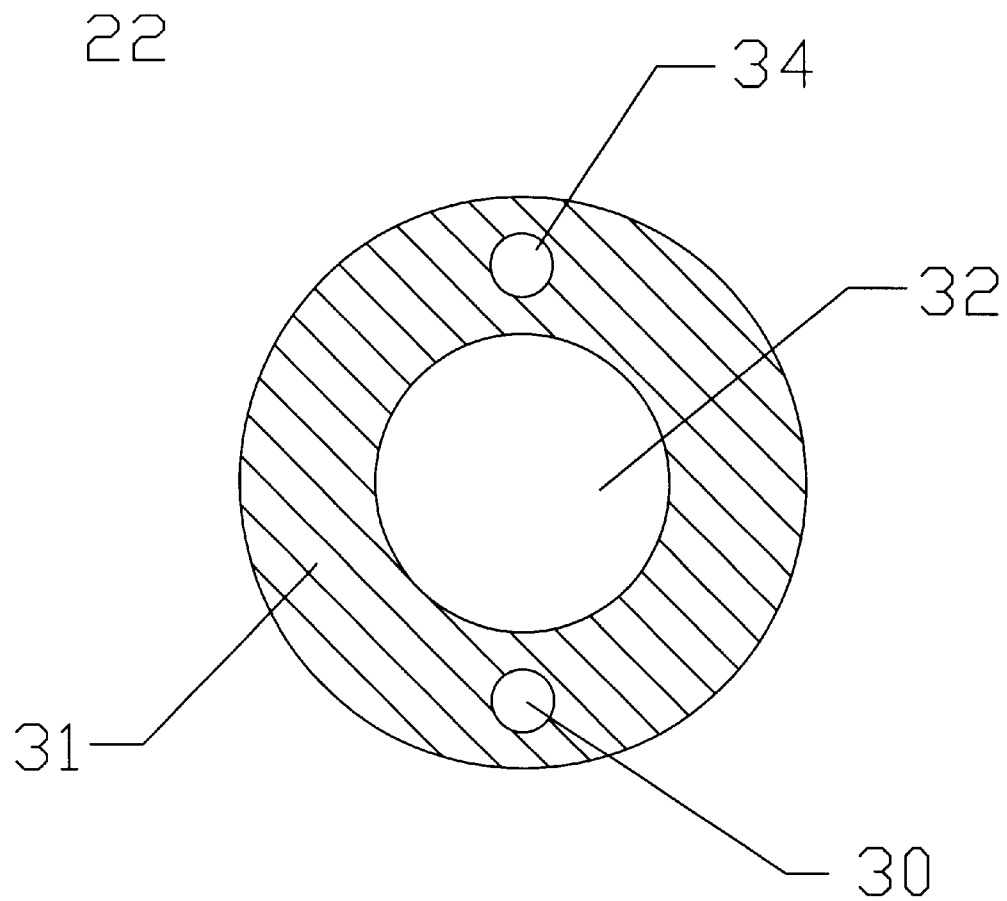
FIG. 2 illustrates a lateral cross-section of a multi-lumen tube for construction of the cannula according to aspects of an embodiment of the invention.

FIG. 2 shows the cross-section of the connection tubing 22. The connection tubing 22 is multi-lumen tubing and comprises, at minimum, an infusion lumen 30, a venous drainage lumen 32, an inflation lumen 34, and a wall 31. The connection tubing 22 is preferably made from a polymeric material such as polyvinyl chloride, polyethylene, polypropylene, polyurethane and the like. Preferably, the tubing 22 is transparent.

Figure 3:
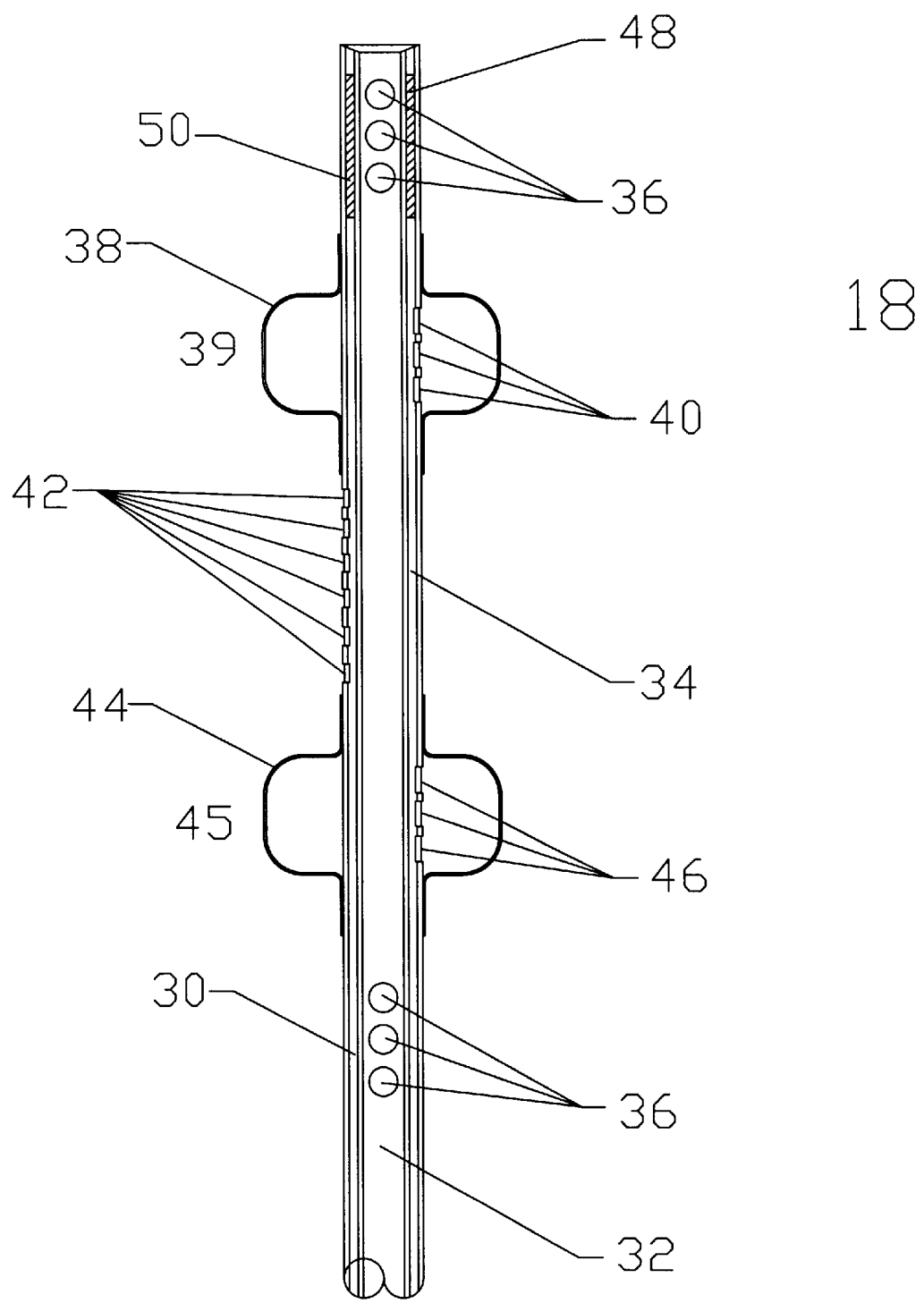
FIG. 3 illustrates, in detail, a longitudinal cross-section of the distal tip of the cannula of FIG. 1 according to aspects of an embodiment of the invention.

FIG. 3 illustrates the distal tip 18 of the catheter 10 of FIG. 1 in detail. The distal tip 18 is an extension of the connecting tubing 22 and comprises the infusion lumen 30, the venous drainage lumen 32 and the inflation lumen 34. Additionally, the distal tip 18 comprises a plurality of venous drainage ports 36, a distal or first occlusion device 39, a plurality of cardioplegia infusion port or ports 42, and a proximal or second occlusion device 45. The distal tip 18 further comprises an inflation lumen plug 48 and an infusion lumen plug 50. A cardioplegic drainage lumen may likewise be utilized to adjust cardioplegic perfusion pressures, if needed.

In this preferred embodiment, the first occlusion device 39 comprises a first balloon 38 and a plurality of first balloon inflation ports 40. The second occlusion device 45 comprises a second balloon 44 and a plurality of second balloon inflation ports 46.

The venous drainage ports 36 are openings in the drainage lumen 32 and connect the venous drainage lumen 32 with the exterior of the cannula 10. There is no communication between the venous drainage lumen 32 and the other cannula lumens 30 and 34. The venous drainage ports 36 are preferably located more proximally than the second balloon 44 and/or more distally than the first balloon 38 on the cannula 10.

The balloon inflation ports 40 and 46 are located on the inflation lumen 34. The inflation lumen 34 is isolated from the other cannula lumens 30 and 32. The first balloon 38 and the second balloon 44 are located over the first balloon inflation ports 40 and the second balloon inflation ports 46, respectively. When the balloon inflation fluid flows through the inflation ports 40 and 46 from the inflation lumen 34, the balloons 38 and 44 inflate.

The cardioplegia infusion port(s) 42 are openings on the infusion lumen 30. The infusion lumen 30 is isolated from the other lumens 32 and 34. The cardioplegia infusion ports 42 are located between the balloons 38 and 44 such that cardioplegia solution is infused between the balloons 38 and 44 and is directed into the right atrium of the heart where it subsequently passes into the coronary arteries by way of the coronary sinus.

Figure 4:
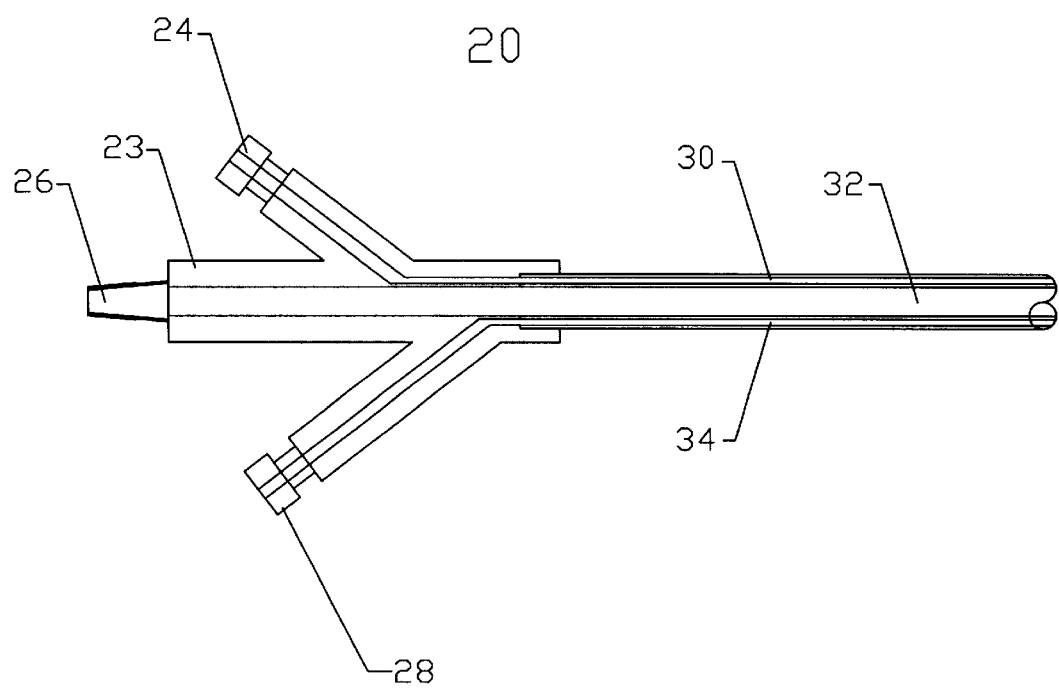
FIG. 4 illustrates, in detail, a longitudinal cross-section of the proximal end of the cannula of FIG. 1 according to aspects of an embodiment of the invention.

FIG. 4 shows the proximal end 20 of the cannula 10 of FIG. 1 in detail. The proximal end 20 is an extension of the connecting tube 22 and comprises the cardioplegic infusion lumen 30, the venous drainage lumen 32, and the inflation lumen 34. The proximal end 20 additionally comprises the manifold 23, which comprises the cardioplegia infusion adapter 24, the venous drainage collection adapter 26 and the balloon inflation adapter 28. The cardioplegia infusion adapter 24 connects to the infusion lumen 30. The venous drainage collection adapter 26 connects to the drainage lumen 32 and the balloon inflation adapter 28 connects to the inflation lumen 34.

Figure 5:
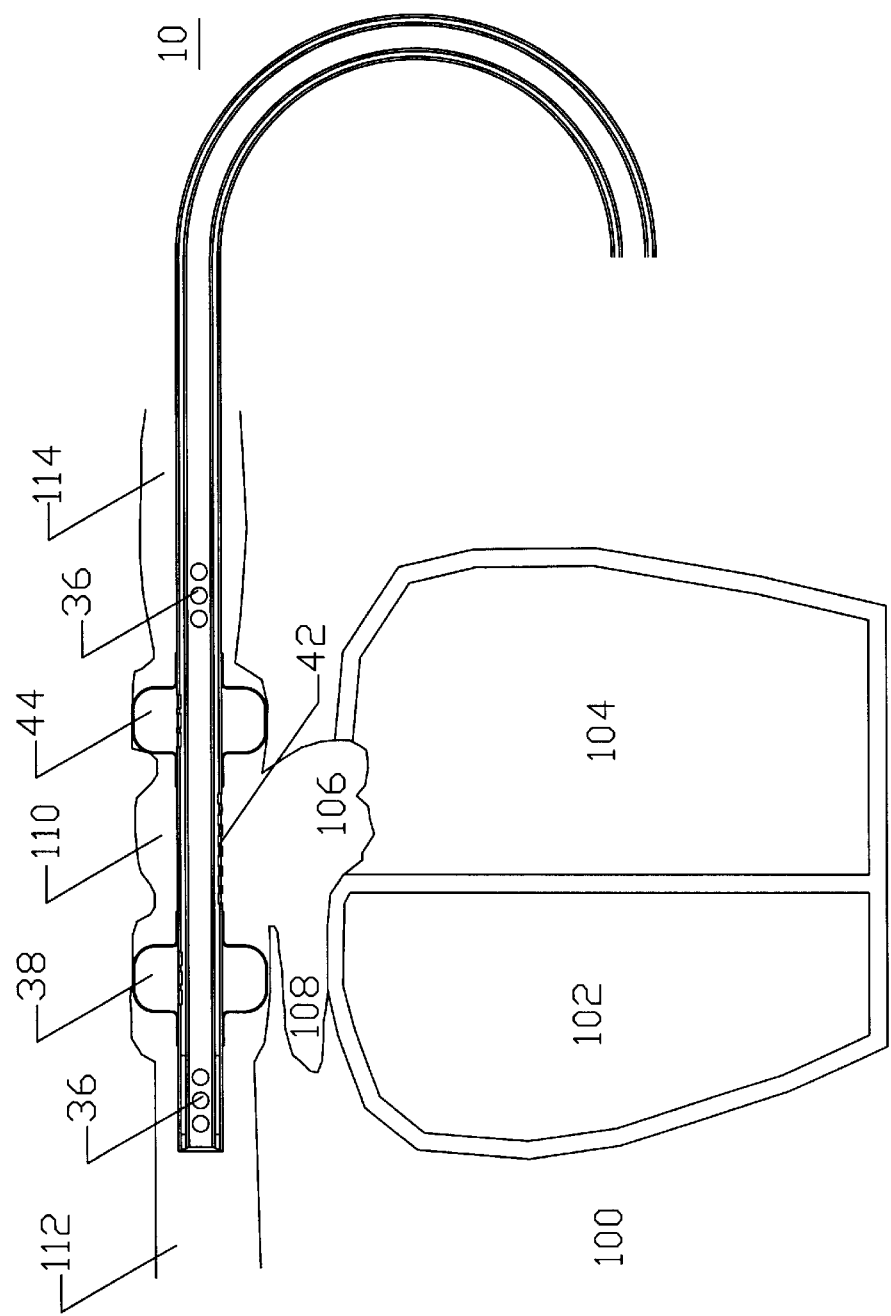
FIG. 5 shows the placement of the cannula of the present invention in the heart for venous drainage and retrograde perfusion according to aspects of an embodiment of the invention.

FIG. 5 illustrates the placement of the cannula 10 of the present invention in a heart 100 during retrograde perfusion. The heart 100 comprises a left ventricle 102, a right ventricle 104, a tricuspid valve 106, a coronary sinus 108, a right atrium 110, an inferior vena cava 112, and a superior vena cava 114.

During normal operation of the heart, blood returning from the tissues of the body passes through peripheral veins into the superior 114 and inferior vena cava 112 and into the right atrium 110. The coronary sinus 108 is the region of the heart 100 where blood exits the coronary vascular circuit and passes back into the right atrium 110. The coronary sinus 108 is located in close proximity to the inferior vena cava's entry into the right atrium 110. Blood leaving the coronary circulation by way of the coronary sinus 108 joins the venous blood from the vena cava 112 and 114 in the right atrium 110. The venous blood flows through the right atrium 110 and is pumped by the right ventricle 104 into the lungs where it is oxygenated and carbon dioxide is removed. The oxygen-rich blood then passes into the left atrium and left ventricle 102 where it is then pumped into the systemic circulation to nourish the organs and tissues of the body. The coronary ostea, or entrance to the coronary arteries, are located at the root of the aorta, just downstream of the aortic valve.

When the heart 100 is placed on cardiopulmonary bypass, blood is removed from the venous circulation at the inferior vena cava 112 and superior vena cava 114 and is routed to an oxygenator that adds oxygen and removes carbon dioxide. The oxygenated blood is pumped back into the patients systemic circulation so tissues can be perfused while the heart is being surgically repaired.

The cannula 10 of the present invention serves the triple function of blocking venous blood from entering the right heart during surgery, removing the venous blood from the vena cava so that it may be extracorporeally oxygenated and pumped back to the patient, and infusing cardioplegia solution into the heart in a retrograde direction during the surgical repair procedure.

Referring to FIGS. 1,3,4, and 5, the physician makes an incision in the jugular vein, for example, and inserts the distal tip 18 of the catheter or cannula 10 into the incision. The catheter 10 is threaded into the vein, advanced into the vena cava 112 and 114, and positioned, with the aid of fluoroscopy, for example, such that the balloons 38 and 44 are located in the inferior vena cava 112 and superior vena cava 114, respectively. The cardioplegia infusion ports 42 are located at the entrance to, or inside of, the right atrium 110 and the drainage ports 36 are located in the superior vena cava 114 and inferior vena cava 112, proximal or upstream of the balloons 38 and 44.

Next, the balloon inflation system 16 is activated. Balloon inflation is accomplished by driving balloon inflation fluid from the balloon inflation system 16, through the balloon inflation adapter 28, into the balloon inflation lumen 34, through the balloon inflation ports 40 and 46 and into the balloons 38 and 44. The inflation lumen plug 48 prevents the balloon inflation fluid from escaping from the distal end of the inflation lumen 34. This infusion of balloon inflation fluid causes the balloons 38 and 44 to inflate and occlude the entrance of the right atrium 110 from the superior vena cava 114 and the inferior vena cava 112. Because of this occlusion, blood is prevented from flowing from the superior vena cava 114 and the inferior vena cava 112 into the right atrium 110 of the heart 100, and must exit via the drainage ports 36 of the cannula 10. The blood passes through the cannula 10 and on into the venous reservoir of the cardiopulmonary bypass system.

The cardioplegia infusion system 12 is next activated. The cardioplegia solution flows from the cardioplegia infusion system 12, through the cardioplegia infusion adapter 24, into the infusion lumen 30, through the cardioplegia infusion ports 42, and into the right atrium 110 where, under moderate pressure, the cardioplegia solution enters the coronary sinus 108 and the right ventricle 104. In order for cardioplegic solution to enter the coronary sinus 108 in a retrograde fashion, the right atrium 110 and ventricle 104 must be pressurized, which necessitates occlusion of the pulmonary artery root. The pulmonary artery thus is typically cross-clamped to prevent perfusion of the lungs during surgery. The infusion lumen plug 50 prevents the cardioplegia solution from escaping from the distal end of the infusion lumen 30. The cardioplegia solution arrests the beating of the heart 100 by interfering with the sodium potassium cycle of the cardiac muscle cells.

In addition, the venous drainage collection system 14 is activated. Any blood in the superior vena cava 114 and inferior vena cava 112 flows through the drainage ports 36, into the drainage lumen 32, through the drainage collection adapter 26, and into the drainage collection system 14. The drainage collection system 14 collects the venous blood.

This blood is, in most cases, routed to a venous reservoir of a cardiopulmonary bypass system where it then passes into an oxygenator and heat exchanger where it, respectively, undergoes removal of carbon dioxide and addition of oxygen and undergoes heat transfer. The oxygenated blood is pumped back into the patient's systemic circulation via an arterial cannula placed in a systemic artery distal to the aortic valve.

The surgeon can now perform the prescribed heart surgery. A single cannula of the present invention provides the infusion, inflation, and drainage functions, which eliminates the need for the multiple cannulae currently used for open-heart procedures.

Figure 6:
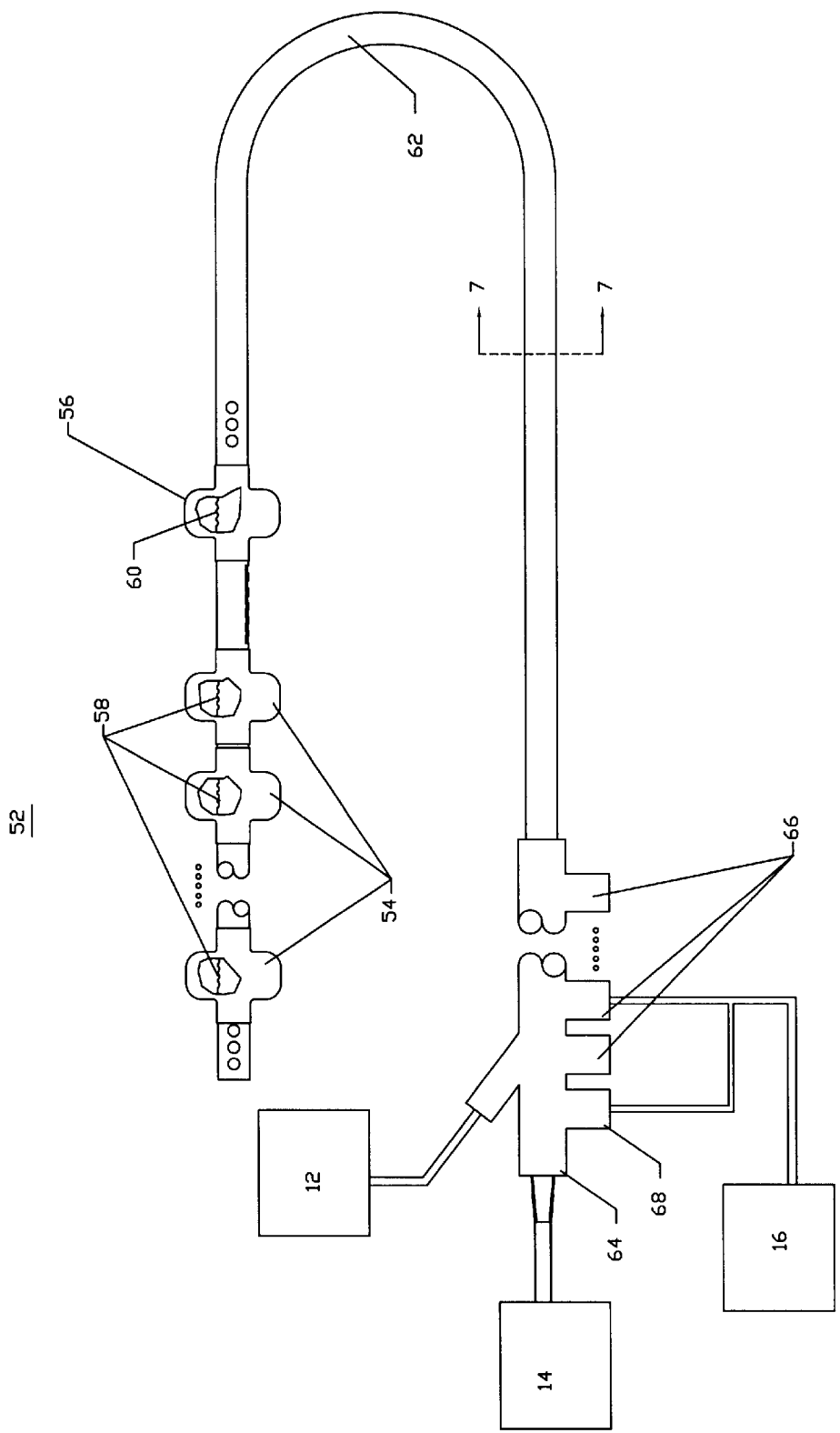
FIG. 6 illustrates, in exterior view, another embodiment of the cannula comprising multiple balloons to accommodate various anatomic differences according to aspects of an embodiment of the invention. Cutouts on the balloons show features on the cannula surface that would normally be hidden by the balloons.

Referring to FIG. 5, patients have different spacing between the entrance of the inferior vena cava 112 into the right atrium 110 and the entrance of the superior vena cava 114 into the right atrium 110. A one-size-fits-all catheter 10 may not be optimum for use in all patients. FIG. 6 shows a more preferred embodiment of the catheter, which compensates for anatomic differences between patients. The operation of cardioplegia infusion and drainage collection are the same as that described earlier for the cannula 10.

Referring to FIG. 6, the catheter or cannula 52 comprises a plurality of first balloons 54, a second balloon 56, a plurality of first balloon inflation port sets 58, a plurality of second balloon inflation ports 60, and a length of connecting tubing 62. The catheter 52 also comprises a manifold 64, which comprises a plurality of first balloon inflation adapters 66 and a second balloon inflation adapter 68. The catheter is connected to the cardioplegia infusion system 12, the venous drainage collection system 14, and the balloon inflation system 16.

Figure 7:
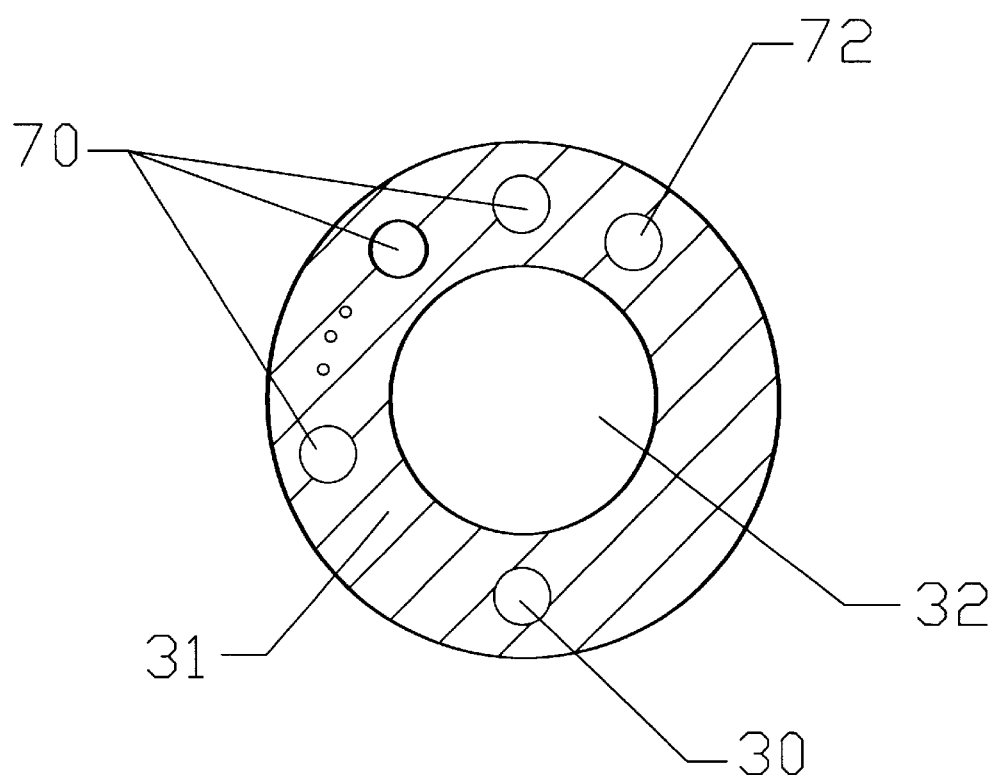
FIG. 7 illustrates a lateral cross-section of a multi-lumen tubing for construction of the cannula of FIG. 6 according to aspects of an embodiment of the invention.

FIG. 7 illustrates a cross section of multi-lumen connection tubing 62 for the construction of the catheter 52 of FIG. 6. The tubing 62 comprises a plurality of first balloon inflation lumen 70, a second balloon inflation lumen 72, the infusion lumen 30, the drainage lumen 32, and the wall 31.

Referring to FIGS. 6 and 7, the balloon inflation system 16 connects to the catheter 52 through the first balloon inflation adapters 66 and the second balloon inflation adapter 68. Each first balloon inflation adapter 66 connects to one first balloon inflation lumen 70. The second balloon inflation adapter 68 connects to the second balloon inflation lumen 72. Each set of first balloon inflation ports 58 is located on one first balloon inflation lumen 66. The second balloon inflation ports 60 are located on the second balloon inflation lumen 72. Each first balloon 54 is positioned over one set of first balloon inflation ports 58, such that when inflation fluid is injected through the selected first balloon inflation ports 58, only the first balloon 54 over the selected first balloon inflation ports 58 is inflated. The second balloon 56 is positioned over the second balloon inflation ports 60 such that when balloon inflation fluid is injected through the second balloon inflation ports 60, the second balloon 56 is inflated. Each first balloon inflation adapter 66 has a corresponding first balloon inflation lumen 70, a corresponding set of first balloon inflation ports 58, and a corresponding first balloon 54.

Referring to FIGS. 5 and 6, the physician places the catheter 52 into the right atrium 110. The physician places the second balloon 56 in the entrance of the superior vena cava 114 and the series of first balloons 54 line up in the right atrium 110 and into the inferior vena cava 112. The second balloon 56 is inflated to occlude the superior vena cava 114. Only the first balloon 54 in the plurality of first balloons 54, which is in the entrance of the inferior vena cava 112, corresponding to the correct spacing for the patient's heart, is inflated to occlude the inferior vena cava 112. Balloons 54 and 56 to be inflated are connected to the balloon inflation system 16 through their balloon inflation lumen 70 and 72. The balloon inflation lumen 70 of the balloons 54 selected for non-inflation are simply not connected to the balloon inflation system 16. In this manner, the catheter 52 is optimized for the individual patient's anatomy. The better fit minimizes the chance of the balloons 54 and 56 slipping out of position and leaking venous blood into the heart, with potentially severe complications for the surgery patient.

Preferably, the plurality of balloons are located on the distal end of the catheter's cardioplegia infusion ports 42, although multiple balloons proximal to the cardioplegia inflation ports 42 would also be acceptable. Only the balloons that are spaced correctly to occlude the patient's superior 114 and inferior 112 vena cava are inflated.

In another embodiment for multiple balloon inflation selection, a single balloon inflation lumen may be connected to all of the balloons and to a control rod that selectively opens balloon inflation ports to the correct balloon or balloons. Such a control rod would typically be an axially elongate, torqueable structure running the length of the cannula tubing. By rotating or axially moving the control rod by grasping a projection at the proximal end of the cannula, inflation ports would be selectively opened between the balloon inflation lumen and the balloon to be inflated. Markings on the control rod would indicate which balloons were being inflated or which spacing was being chosen. Again, only the balloons correctly spaced to occlude the patient's vena cava are inflated. Other balloons would not be inflated because their ports would not have been selectively opened.

In yet another embodiment of the cannula 10, the distal tip 18 comprises an accordion-like or telescoping structure between the occlusion devices 39 and 45, and a control rod. The accordion-like or telescoping structure allows the length of the cannula 10 to be adjusted so that the occlusion devices 39 and 45 fit the spacing between the patient's superior vena cava 114 and inferior vena cava 112. This accordion-like structure is a longitudinally flexible area of the cannula 10 with corrugations to allow for compression or expansion in length. The control rod extends from the distal tip 18 of the cannula 10 to the proximal end 20. The control rod is linked to the cannula 10 such that pushing or pulling the control rod relative to the proximal end 20 increases or decreases the length of the cannula 10. The control rod is locked into place with a locking device when the correct spacing between the occlusion devices 39 and 45 is achieved. A telescoping structure could be used in place of the accordion-like structure to allow for cannula length adjustment using the control rod.

In yet another embodiment, the balloon inflation adapter 28 is connected to the cardioplegia infusion system 12. In this embodiment, the cardioplegia solution is used in the cardioplegia infusion system 12 to arrest the heart and in the balloon inflation system 16 to inflate the balloons 38 and 44 or 54 and 56. Typically, cardioplegia solution is infused at a pressure of around 20 mmHg. The balloons 38, 44, 54, and 56 may be inflated with an internal pressure of 20 mmHg and this pressure may be derived from the pressure of the cardioplegia solution. This embodiment has the advantage of reduced complexity and simplified pressure limiting.

The balloons 38 and 44 are only one way of occluding the vena cava 112 and 114. Another embodiment of the occlusive structures 39 and 45 comprises one or more external tourniquets. One or more tourniquets may be applied external to the vena cava 112 and 114 to seal the vena cava 112 and 114 to the cannula 10 and prevent cardioplegia solution from escaping the environs of the right atrium entry 110 to the coronary sinus 108.

A further embodiment of the occlusive structures 39 and 45 comprises umbrella mechanisms, which open up to occlude the vena cava. Opening and closing of the umbrellas would be accomplished using a control rod extending along the length of the catheter and out the proximal end of the catheter where it could be grasped.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

I claim:

1. A method of cannulating a patient's heart during cardiopulmonary bypass comprising the steps of:
    inserting a cannula into a venous system of the patient;
    positioning the cannula so that said cannula traverses a right atrium and extends into both a superior and an inferior vena cava;
    enabling an occlusion device in each of the superior and inferior vena cava;
    draining venous blood from the vena cava and;
    infusing cardioplegia solution into the right atrium of the heart, and infusing said cardioplegia solution, retrograde, into the coronary sinus without cannulating the coronary sinus,
wherein all steps are performed by use of a single cannula.

2. The method of claim 1 wherein the cannula is routed to the heart, through the veins, from the jugular vein.

3. The method of claim 1 further comprising the step of measuring the pressure in the right atrium of the heart.

4. The method of claim 1 wherein the cardioplegia solution is directed into the coronary sinus by the occlusion devices in the superior and inferior vena cava.

5. The method of claim 1 wherein the occlusion devices in the superior and inferior vena cava are balloons.

6. The method of claim 1 wherein the distance between the occlusion devices in the superior and inferior vena cava is adjustable.

* * * * *